United States Patent [19]
O'Hara et al.

[11] Patent Number: 6,093,179
[45] Date of Patent: Jul. 25, 2000

[54] APPARATUS AND METHOD FOR PLACEMENT OF A PERCUTANEOUS ENDOSCOPIC GASTROSTOMY TUBE

[75] Inventors: Derek P. O'Hara, Tourlestrane; Brendan J. Duggan, Strandhill, both of Ireland; Gail M. Comer, Libertyville, Ill.; Donald J. Goldhardt, Grove City, Ohio

[73] Assignee: Abbott Laboratories, Abbott Park, Ill.

[21] Appl. No.: 09/010,411

[22] Filed: Jan. 21, 1998

[51] Int. Cl.[7] ........................ A61M 31/00; A61M 5/178
[52] U.S. Cl. ........................ 604/500; 604/159; 604/164
[58] Field of Search ........................ 604/96, 93, 170, 604/159, 49, 164, 280; 606/108; 128/898

[56] References Cited

U.S. PATENT DOCUMENTS

| | | | |
|---|---|---|---|
| 3,995,628 | 12/1976 | Gula et al. | 128/214.4 |
| 4,342,313 | 8/1982 | Chittenden . | |
| 4,573,576 | 3/1986 | Krol . | |
| 4,668,225 | 5/1987 | Russo et al. . | |
| 4,713,059 | 12/1987 | Bickelhaupt et al. . | |
| 4,781,704 | 11/1988 | Potter | 604/270 |
| 5,139,486 | 8/1992 | Moss . | |
| 5,243,679 | 9/1993 | Sharrow et al. . | |
| 5,366,444 | 11/1994 | Martin | 604/159 |

FOREIGN PATENT DOCUMENTS

WO 97/11736  4/1997  WIPO .
WO 97/47351  12/1997  WIPO .

*Primary Examiner*—Wynn Wood Coggins
*Assistant Examiner*—Michael T. Hayes
*Attorney, Agent, or Firm*—Brian R. Woodworth; Daniel J. Hulseberg

[57] ABSTRACT

A method for placing a feeding tube placement wire in a patient. The method includes the step of providing a placement wire dispenser. The dispenser includes a rotatable placement wire receptacle that defines a placement wire outlet. The dispenser further includes a tube extending outwardly from the placement wire receptacle. The tube defines a placement wire inlet that is in communication with the placement wire outlet of the receptacle. A placement wire is wound about the receptacle, and is in mechanical engagement with the receptacle, such that rotation of the placement wire receptacle causes a first end of the placement wire to be advanced through the placement wire outlet, through the placement wire inlet of the tube, and through the tube. A first end of the tube is constructed for insertion through a patient's abdominal wall and into a patient's stomach. The method further includes the step of placing the first end of the tube through a patient's abdominal wall and into a patient's stomach. Rotational movement is imparted to the receptacle so as to advance the placement wire through the placement wire outlet, through the placement wire inlet, through the tube, and into a patient's stomach.

17 Claims, 2 Drawing Sheets

APPARATUS AND METHOD FOR PLACEMENT OF A PERCUTANEOUS ENDOSCOPIC GASTROSTOMY TUBE

TECHNICAL FIELD

This invention relates to an improved apparatus useful in the placement of a percutaneous endoscopic gastrostomy tube. In particular, the present invention is directed to a introducer attached to a receptacle about which a placement wire is positioned. Following insertion of the introducer into a selected portion of a patient's gastrointestinal tract, the placement wire is inserted into a patient through the introducer by rotating the receptacle, thereby advancing the wire through the introducer.

BACKGROUND OF THE INVENTION

Gastrostomy and jejunostomy tubes are used to deliver nutritional products to the gastrointestinal tract of a patient having difficulty ingesting food. Gastrostomy tubes deliver the nutritional products percutaneously from an external source, through the patient's abdominal wall, and directly to the patient's stomach, while jejunostomy tubes deliver the nutritional products percutaneously into the patient's jejunum or small bowel. Gastrostomy and jejunostomy tubes are referred to collectively herein as "feeding tubes."

The first step in placing a feeding tube in a patient typically involves the passing of an endoscope down the patient's esophagus in order to view the esophagus and determine whether there are any obstructions or lesions in the esophagus that will inhibit or preclude passage of the feeding tube through the esophagus. The endoscope also is used to examine the interior of the stomach and/or the small bowel. Next, the doctor visually selects the site through which the feeding tube will be introduced into the stomach and transilluminates the selected site by directing light outwardly from the endoscope such that the light shines through the patient's abdominal wall, thereby allowing the doctor to identify the entry site from a point outside of the patient's body. The doctor then inserts a catheter or introducer through the patient's abdominal wall and into the stomach at the selected entry site. A first end of a placement wire is then passed through the introducer and into the stomach. The first end of the wire is grasped using a grasping tool associated with the endoscope, and the endoscope and the placement wire are drawn outwardly from the patient's stomach and esophagus through the patient's mouth. Upon completing this step of the procedure, a second end of the wire remains external to the patient's abdominal wall while the first end of the wire extends outwardly from the patient's mouth.

In one technique for feeding tube placement, the first end of the placement wire is attached to a first end of a feeding tube. Attachment of the feeding tube to the first end of the placement wire is facilitated by a loop on the first end of the placement wire and by a complementary loop on the first end of the feeding tube. By pulling on the second end of the wire positioned external to the patient's abdominal wall, the feeding tube is pulled through the patient's mouth and esophagus, and into stomach. Further pulling of the second end of the wire causes the first end of the feeding tube to exit percutaneously from the stomach through a tract in the abdominal wall formed by the introducer. The feeding tube is pulled outwardly through the tract until a retaining member mounted on the second end of the feeding tube engages the interior of the stomach. This technique is referred to as a "pull" technique.

In an alternative technique for feeding tube placement, a channel defined through the feeding tube is positioned over the wire such that the feeding tube can be pushed along the length of the wire. As the feeding tube is pushed over the wire, it passes through the patient's mouth, esophagus, and stomach until the first end of the feeding tube exits through the incision in the abdominal wall. The feeding tube is then drawn outwardly through the abdominal tract until a retaining member on the second end of the feeding tube engages the interior of the stomach. The wire is then withdrawn from the patient through the feeding tube channel. This technique is referred to as a "push" technique.

Placement wires can have a variety of forms. In one commercially available embodiment, the placement wire is a doubled wire coated with a biocompatible plastic material. However, other forms of placement wires are well known. These placement wires typically are provided in a sterile package for use by a medical professional. For example, the placement wire can be coiled and placed in a sealed pouch. The wire is removed from the pouch immediately prior to placement in a patient. This packaging methodology presents certain disadvantages in that the wire is prone to entanglement during insertion into the patient. Thus, the wire must be carefully manipulated in order to ensure that it is fed properly through the introducer and into the patient. Such manipulation may result in touch contamination of the wire as it is manipulated. Further, in order to ensure that the wire is properly fed into the patient's stomach, it is sometimes necessary to have one person manipulate the wire while a second person feeds the wire into the patient. This need for additional medical personnel increases the cost of placing the feeding tube in the patient.

In a second commercially available embodiment, the wire is a "silk" type pull thread that is loosely coiled in a provided holder. The thread extends through a hole in the holder and can be pulled outwardly from the holder through the hole. As the endoscope is withdrawn through the patient's esophagus, an assistant must carefully pull the thread out of the holder and allow it to feed through the catheter. This embodiment also presents certain disadvantages due to the fact that an assistant is required in order to manipulate and feed the thread into the catheter. In addition, it typically is necessary to create a knot in the end of the thread before attaching it to a feeding tube. In some cases, creation of this knot can be difficult due to the physical characteristics of the silk thread after it has been drawn through the patient's stomach, esophagus, and mouth.

In another commercially available embodiment, the placement wire is retained in a coil of rigid tubing. The wire can be difficult to manipulate and therefore may require the presence of an assistant to withdraw the wire from the coiled tubing. However, this embodiment does tend to reduce tangling of the placement wire during placement of the wire in the patient.

In yet another commercially available embodiment, the placement wire is provided in a circular dispenser. As is the case with each of the other commercially available embodiments, the wire can be difficult to dispense from the circular dispenser, thereby requiring the presence of an assistant. However, this embodiment also tends to minimize tangling of the placement wire.

It is preferable to provide a placement wire in such a way that (a) the possibility of entanglement of the wire is minimized; (b) the possibility of touch contamination of the wire is minimized; and (c) withdrawal of the wire from its packaging does not require additional personnel. The present invention addresses each of these.

SUMMARY OF THE INVENTION

The present invention is directed to a method for placing a feeding tube placement wire in a patient. The method includes the step of providing a placement wire dispenser. The dispenser includes a rotatable placement wire receptacle that defines a placement wire outlet. The dispenser further includes a tube extending outwardly from the placement wire receptacle. The tube defines a placement wire inlet that is in communication with the placement wire outlet of the receptacle. A placement wire is wound about the receptacle, and is in mechanical engagement with the receptacle, such that rotation of the placement wire receptacle causes a first end of the placement wire to be advanced through the placement wire outlet, through the placement wire inlet of the tube, and through the tube. A first end of the tube is constructed for insertion through a patient's abdominal wall and into a patient's stomach. The method further includes the step of placing the first end of the tube through a patient's abdominal wall and into a patient's stomach. Rotational movement is imparted to the receptacle so as to advance the placement wire through the placement wire outlet, through the placement wire inlet, through the tube, and into a patient's stomach.

The present invention further includes a placement wire dispenser. The dispenser includes a rotatable placement wire receptacle that defines a placement wire outlet. The dispenser further includes a tube extending outwardly from the placement wire receptacle. The tube defines a placement wire inlet that is in communication with the placement wire outlet of the receptacle. A placement wire is wound about the receptacle, and is in mechanical engagement with the receptacle, such that rotation of the placement wire receptacle causes a first end of the placement wire to be advanced through the placement wire outlet, through the placement wire inlet of the tube, and through the tube. A first end of the tube is constructed for insertion through a patient's abdominal wall and into a patient's stomach.

The present invention further is directed to a feeding tube placement kit. The kit includes a placement wire dispenser. The dispenser includes a rotatable placement wire receptacle that defines a placement wire outlet. The dispenser further includes a tube extending outwardly from the placement wire receptacle. The tube defines a placement wire inlet that is in communication with the placement wire outlet of the receptacle. A placement wire is wound about the receptacle, and is in mechanical engagement with the receptacle, such that rotation of the placement wire receptacle causes a first end of the placement wire to be advanced through the placement wire outlet, through the placement wire inlet of the tube, and through the tube. A first end of the tube is constructed for insertion through a patient's abdominal wall and into a patient's stomach. The kit further includes a feeding tube having a first end portion and a second end portion. The feeding tube defines a feeding lumen therethrough. A retention member is disposed on the second end portion of the feeding tube.

The present invention also is directed to a feeding tube adaptor having an outlet conduit and an inlet conduit. An exterior surface of the outlet conduit is configured such that it has a first section having an increasing circumferential dimension from an outlet end of the adaptor to an inlet end of the adaptor. The exterior surface of the outlet conduit further is configured such that it has a second section having a decreasing circumferential dimension from an outlet end of the adaptor to an inlet end of the adaptor. The first and second sections of the exterior surface of the outlet conduit define a tube retention member.

BRIEF DESCRIPTION OF THE DRAWINGS

In the accompanying drawings that form part of the specification, and in which like numerals are employed to designate like parts throughout the same.

DETAILED DESCRIPTION

While this invention is susceptible of embodiment in many different forms, this specification and the accompanying drawings disclose specific embodiments as examples of the invention. The invention is not intended to be limited to the embodiments so described. The scope of the invention is pointed out in and defined by the appended claims.

The figures illustrating the apparatus show some elements that are known and that will be recognized by one skilled in the art. The detailed descriptions of such elements are not necessary to an understanding of the invention, and accordingly, are herein presented only to the degree necessary to facilitate an understanding of the novel features of the present invention.

The present invention is practiced with certain conventional components the details of which, although not fully illustrated or described, will be apparent to those having skill in the art and an understanding of the necessary functions of such components.

The method of the invention will be described herein in the context of the accompanying figures which depict a method for placing a feeding tube percutaneously into the stomach of a patient. However, it will be appreciated by one of ordinary skill in the art that the method of the present invention can be employed for the purposes of placing feeding tubes into other preselected sections of the gastrointestinal tract of a patient, e.g., the small bowel. Accordingly, the detailed description set forth herein is intended to cover methods for placing feeding tubes into any preselected section of the gastrointestinal tract of a patient, including, but not limited to, the stomach and the small bowel.

Figure 1:
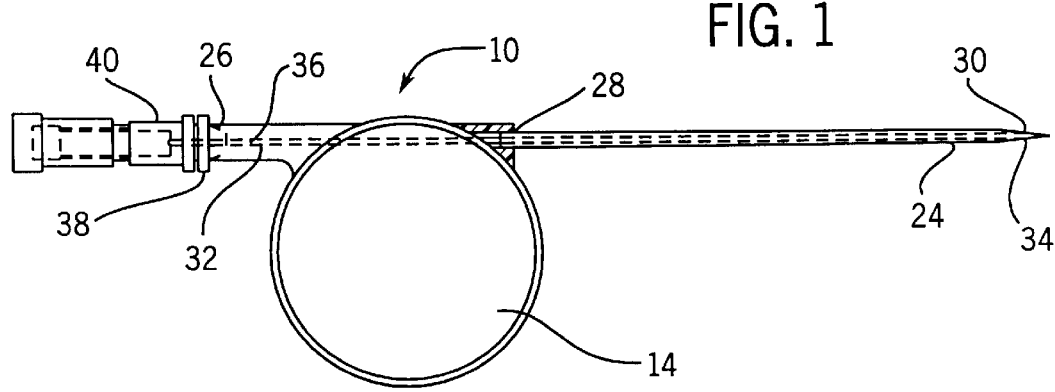
FIG. 1 is a perspective view of a placement wire dispenser constructed in accordance with the present invention.
Figure 2:
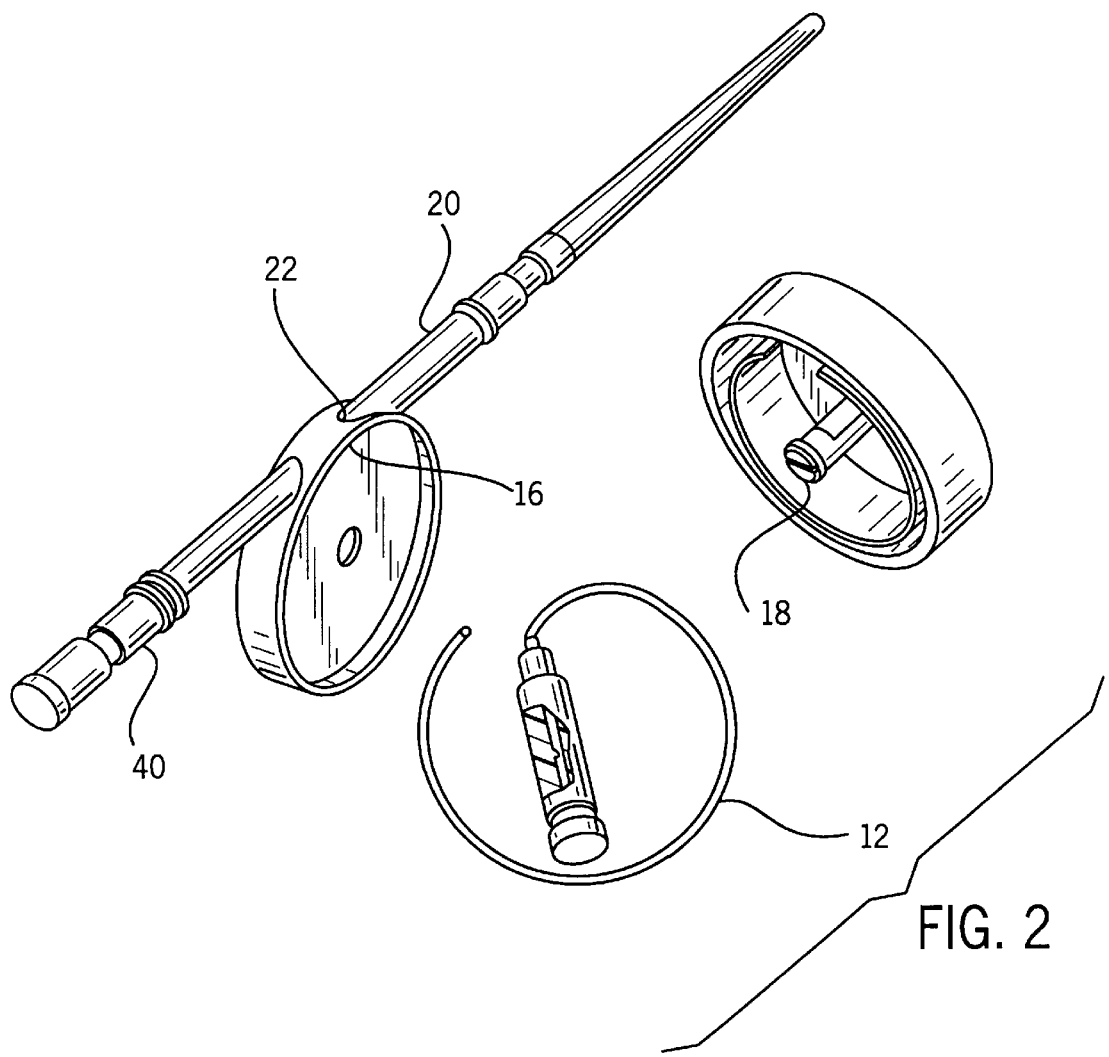
FIG. 2 is an exploded view of a placement wire dispenser constructed in accordance with the present invention.
Figure 3:
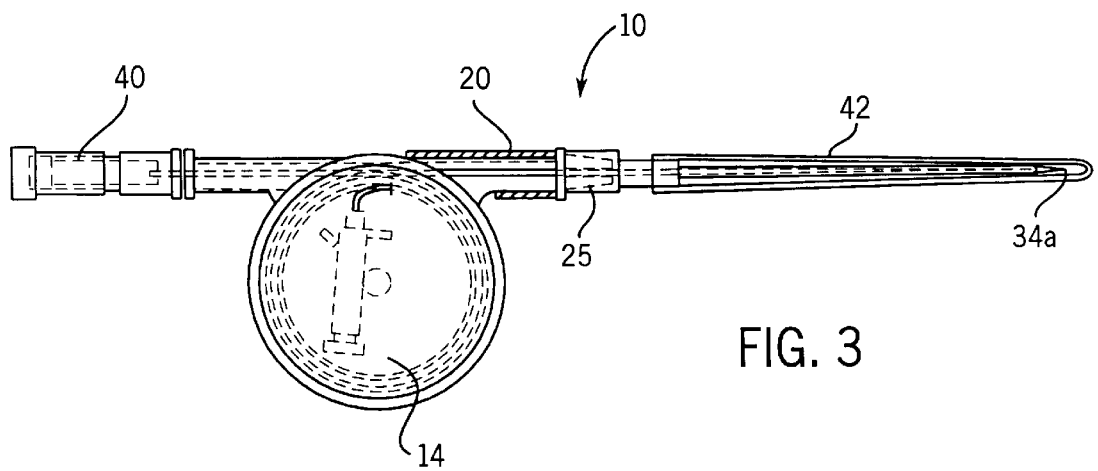
FIG. 3 is a second perspective view of a placement wire dispenser constructed in accordance with the present invention.
Figure 4:
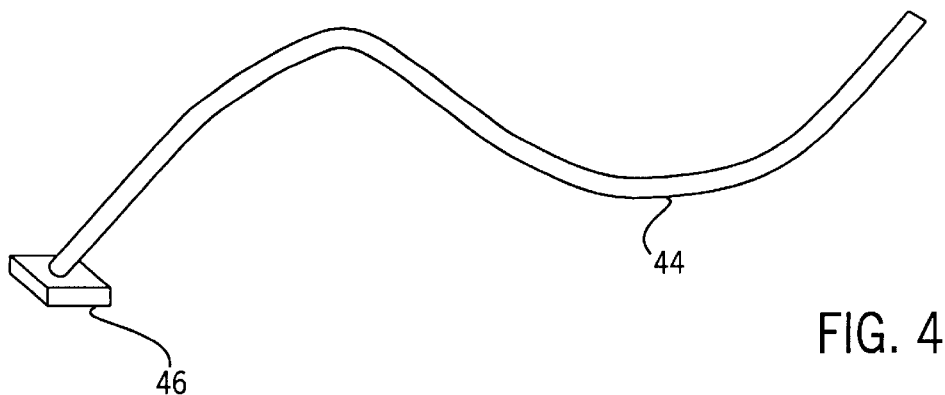
FIG. 4 is a perspective view of a feeding tube constructed in accordance with the present invention.
Figure 5:
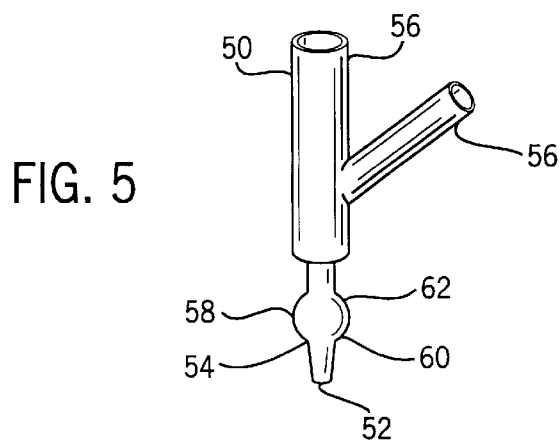
FIG. 5 is a perspective view of an adaptor constructed in accordance with the present invention.

Dispenser 10 constructed in accordance with the present invention is generally depicted in FIG. 1. Dispenser 10 is constructed substantially in accordance with the teachings set forth in U.S. Pat. No. 4,342,313 which is incorporated herein by reference. U.S. Pat. No. 4,342,313 is assigned of record to Abbott Laboratories, the assignee of the invention disclosed and claimed herein. Applicants also hereby incorporate herein by reference the teachings of U.S. Ser. No. 08/733,900 filed Oct. 18, 1996 which was a continuation of U.S. Ser. No. 08/365,398 filed Dec. 28, 1994. These applications also are assigned of record to Abbott Laboratories.

Dispenser 10 includes a placement wire 12 wound about a receptacle 14. Placement wire 12 can be constructed of a variety of known, biocompatible materials and can have a variety of known configurations useful in the placement of percutaneous endoscopic gastrostomy and jejunostomy tubes. In a preferred embodiment, wire 12 includes a pair of wires coated with a biocompatible, plastic material. Receptacle 14 preferably contains placement wire 12 therein such that placement wire 12 is not exposed to an external environment of receptacle 14 until it is dispensed therefrom, as described in detail herein. Receptacle 14 defines wire outlet 16 therethrough. Wire outlet 16 is configured such that placement wire 12 can be passed therethrough, as explained in detail herein.

Placement wire 12 is in mechanical engagement with receptacle 14 such that rotation of receptacle 14 causes placement wire 12 to rotate and advance outwardly from receptacle 14. One of ordinary skill in the art will appreciate that a variety of methods can be used to mechanically engage placement wire 12 with receptacle 14 such that rotation of receptacle 14 will cause wire 12 to be dispensed therefrom. The present invention is intended to encompass all such methodologies. A spindle or handle 18 can be mechanically connected to receptacle 14 in order to facilitate manual rotation of receptacle 14.

A tubular portion 20 is mounted on receptacle 14 as depicted in FIG. 1. Tubular portion 20 defines wire inlet 22 therethrough. Wire inlet 22 is configured such that placement wire 12 can be passed therethrough. Wire inlet 22 and wire outlet 20 are disposed such that they are in communication with one another, i.e., such that placement wire 12 will pass through wire outlet 16, through wire inlet 22, and into tubular portion 20 when receptacle 14 is rotated. Tubular portion 20 has a first end portion 24 and a second end portion 26. In the embodiment of the present invention depicted in FIG. 1, both first end portion 24 and second end portion 26 are open such that channel 28 defined by tubular portion 20 is open to an external environment of tubular portion 20 at first end portion 24 and second end portion 26. However, it will be appreciated that second end portion 26 can be closed such that channel 28 is not open to an external environment of tubular portion 20 without departing from the spirit of the present invention. This will be explained in greater detail below.

First end portion 24 of tubular portion 20 can be constructed such that it has a substantially flat terminal end 30, as depicted in FIG. 1. In the embodiment depicted in FIG. 1, piercing member 32 is provided and is constructed such that it can be inserted through channel 28 of tubular portion 20 from second end portion 26 to first end portion 24. It will be appreciated that second end portion 26 of tubular portion 20 must be open to an external environment of tubular portion 20 in this embodiment of the present invention in order to permit piercing member 32 to be inserted therein. Piercing member 32 is constructed such that piercing tip 34 thereof is disposed outwardly from terminal end 30 when piercing member 32 is properly positioned within tubular portion 20. Piercing member 32 can be solid. However, in the embodiment of the present invention depicted in the accompanying figures, piercing member 32 defines channel 36 therethrough.

Piercing member 36 has a hub end 38 opposite piercing tip 34. Hub member 40 is mounted on hub end 38. Hub member 40 is configured such that selected instruments can be attached thereto. For example, hub member 40 can be constructed such that it can be fluidly connected to a source of pressurized air and such that pressurized air can be directed through channel 36 after piercing tip 34 has been positioned in a patient's stomach, thereby facilitating insufflation of a patient's stomach. Hub member 40 can be configured such that it provides a variety of known connections, including, but not limited to, threading connections, luer connections, and locking luer connections.

It will be appreciated that piercing member 32 can be omitted from the present invention in certain embodiments. For example, first end portion 24 of tubular portion 20 can be constructed such that it can be inserted directly through a patient's abdominal wall and into a patient's stomach, thereby obviating the need for piercing member 32. That is, a piercing tip 34a can be provided on first end portion 24 of tubular portion 20 where the piercing tip is constructed such that it will penetrate through a patient's abdominal wall and into a patient's stomach. In another alternative embodiment, first end portion 24 is substantially flat, as depicted in the accompanying figures. It will be appreciated that first end portion 24 of tubular portion 20 can be inserted through a dilator, an introducer, or a catheter of known constructed that has been inserted through a patient's abdominal wall and into a patient's stomach. In this way terminal end 30 of tubular portion 20 can be positioned in a patient's stomach without the use of piercing member 32 and without the presence of a piercing tip on tubular portion 20. It is to be appreciated that in some cases it may be possible to insert first end portion 24 of tubular portion 20 through a patient's abdominal wall and into a patient's stomach without the use of a piercing member, a piercing tip, a dilator, an introducer, and/or a catheter. If piercing member 32 is not used, it is not necessary for second end portion 26 of tubular portion 20 to provide communication between channel 28 and an external environment of tubular portion 20.

If piercing member 32 is used, or if first end portion 24 of tubular portion 20 includes piercing tip 34a, protective sheath 42 can be provided in order to prevent piercing tip 34, 34a from inadvertently piercing the skin of a medical professional and/or a patient. In the embodiment depicted in the accompanying figures, sheath 42 is a substantially tubular member configured to surround piercing tip 34, 34a. However, it will be appreciated that sheath 42 can have a variety of known configurations without departing from the scope of the present invention.

In a preferred embodiment of the present invention, a one way fluid flow valve 25 is disposed in channel 28 of tubular portion 20 One way fluid flow valve 25 is constructed to impede the flow of fluid, e.g., air, outwardly from the patient through tubular portion 20. One way fluid flow valve 25 is configured such that it permits the movement of placement wire 12 therethrough as wire 12 is advanced from receptacle 14 through tubular portion 20 and into a patient. One way fluid flow valve 25 can have a variety of known configurations without departing from the scope of the present invention set forth in the appended claims. In one embodiment of the present invention, one way fluid flow valve 25 is a duckbilled valve of known construction.

Placement of a feeding tube is facilitated through the use of dispenser 10 of the present invention. In use, dispenser 10 as described herein is provided. A medical professional urges first end portion 24 of tubular portion 20 inwardly through a patient's abdominal wall and into a patient's stomach. In one embodiment of the method of the present invention, first end portion 24 does not include piercing tip 34a and piercing member 32 is not used. In this embodiment, first end portion 24 of tubular portion 20 is inserted through a patient's abdominal wall and into a patient's stomach with or without the use of a dilator, introducer, or catheter, subject to the discretion of the medical professional. In a second embodiment, first end portion 24 has piercing tip 34a associated therewith. In a third embodiment, piercing member 32 is provided and is inserted through channel 28 such that piercing tip 34 is extends outwardly from terminal end 30 of tubular portion 30. In each case, first end portion 24 is urged through the patient's abdominal wall and into the patient's stomach.

If desired, the medical professional can insufflate the patient's stomach by directing pressurized air through channel 28 and into a patient's stomach. If piercing member 32 is used, the pressurized air can be directed through channel 36 of piercing member 32 and into the patient's stomach. In particular, the source of pressurized air can be connected to hub member 40 of piercing member 32. If piercing member 32 is not used, and if second end portion 26 of tubular portion 20 provides open communication between channel 28 and an external environment of tubular portion 20, pressurized air can be directed through second end portion 26 of tubular portion 20 and into the patient's stomach through channel 28 of tubular portion 20.

If piercing member 32 is used, it is then withdrawn from channel 28 by pulling on hub end portion 38 thereof until piercing tip 34 is withdrawn from second end portion 26 of tubular portion 20.

Rotational movement is then imparted to receptacle 14 such that placement wire 12 advances through wire outlet 16, through wire inlet 22, through channel 28, and into the patient's stomach. Rotational movement can be imparted manually or through the use of a mechanical means, e.g., an electrical motor.

After placement wire 12 has been positioned in the patient's stomach, it is grasped using a grasping tool and withdrawn through the patient's esophagus and mouth in accordance with known methodologies. First end portion 24 of tubular portion 20 can then be withdrawn from the patient's stomach. A feeding tube 44 of known construction is connected to placement wire 12 and the placement wire 12 and the feeding tube 44 are urged through the patient's esophagus and stomach until the feeding tube 44 passes percutaneously through the patient's abdominal wall. In one embodiment feeding tube 44 is constructed of a polyurethane material, e.g., carbathane. Feeding tube 44 can include a known radio-paque material that enables it to be visualized via X-ray. A retaining member 46 is mounted on a second end portion of feeding tube 44. Retaining member 46 is constructed to prevent the second end portion of feeding tube 44 from passing through the patient's abdominal wall. Retaining member 46 can have a variety of known configurations and can be constructed of a variety of known materials, including, but not limited to, silicone and polyurethane.

It has been found that, under certain adverse conditions, retaining member 46 inadvertently can become detached from feeding tube 44 when feeding tube 44 is constructed of a polyurethane material. This potential problem has been found to be particularly present when feeding tube 44 is constructed of a polyurethane material and retaining member 46 is constructed of a silicone material. This potential problem can be obviated by slip molding retaining member 46 on feeding tube 44. Techniques for slip molding are well known in the art and will not be described herein in detail.

Upon proper placement of feeding tube 44 through the patient's abdominal wall, a first end portion of feeding tube 44 can be cut to an appropriate length. A retaining disc 48 can be placed over the first end portion of the feeding tube 44 in order to prevent undesired inward movement of feeding tube 44 through the patient's abdominal wall. Retaining disc 48 can have a variety of known configurations.

An adaptor 50 can be provided in order to interconnect feeding tube 44 and another in-line feeding element, e.g., a tube extending from a source of enteral nutritional product. In one embodiment, adaptor 50 includes outlet conduit 52 having an exterior surface 54. Adaptor 48 further includes one or more inlet conduits 56. An example of a suitable adaptor 50 is disclosed in U.S. Pat. No. 5,057,093 which is incorporated herein by reference.

In the event that feeding tube 44 is constructed of a polyurethane material, it is preferable that exterior surface 54 of outlet conduit 52 define a retention member 58 thereon which prevents feeding tube 44 from slipping off of exterior surface 54 during use. In a preferred embodiment, retention member 58 includes a first section 60 on exterior surface 54. First section 60 has an increasing circumferential dimension viewed from outlet conduit 52 to inlet conduits 56. Retention member 58 further includes a second section 62 Second section 62 has a decreasing circumferential dimension viewed from outlet conduit 52 to inlet conduits 56. First section 60 and second section 62 can be positioned adjacent to one another as depicted in the accompanying figures, or can be spaced from one another by an intermediate section having a variety of configurations, e.g., a surface of substantially constant circumferential dimension, without departing from the spirit of the present invention.

In another aspect of the present invention, a kit for the placement of a feeding tube is provided. The kit includes dispenser 10 and feeding tube 44 constructed in accordance with the above-discussed embodiments thereof. The kit may further include adaptor 50 constructed in accordance with the above-discussed embodiments.

Although the present invention has been described herein in the context of certain embodiments, it will be appreciated that modifications thereto are possible. Such modifications are intended to be within the scope of the present invention, as defined by the appended claims.

What is claimed is:

1. A method for placing a feeding tube in a patient, said method comprising the steps of:

providing a placement wire dispenser including a rotatable placement wire receptacle and a tube extending outwardly from said placement wire receptacle, said placement wire receptacle defining a placement wire receptacle outlet, said tube defining a placement wire tube inlet, said placement wire receptacle outlet and said placement wire tube inlet disposed in communication with one another, a placement wire wound about said placement wire receptacle, said placement wire being in mechanical engagement with said placement wire receptacle whereby rotation of said placement wire receptacle advances a first end portion of said placement wire through said placement wire receptacle outlet and through said tube, said tube having a first end constructed for insertion through a patient's abdominal wall and into a patient's stomach;

placing said first end of said tube through a patient's abdominal wall and into a patient's stomach;

imparting rotational movement to said placement wire receptacle to advance the first end portion of said placement wire from said placement wire receptacle, through said placement wire receptacle outlet, through said placement wire tube inlet, through said tube, and into a patient's stomach;

grasping the first end portion of said placement wire using a grasping tool inserted through a patient's mouth;

withdrawing the first end portion of said placement wire through a patient's mouth using the grasping tool;

removing the first end of said tube from a patient's abdominal wall;

engaging a first end portion of a feeding tube on the first end portion of said placement wire; and urging said feeding tube through a patient's mouth and stomach using said placement wire until the first end portion of said feeding tube passes percutaneously through a patient's abdominal wall.

2. A method for placing a feeding tube in accordance with claim 1, wherein said first end portion of said tube provided by the providing step includes a piercing tip constructed for insertion through a patient's abdominal wall and into a patient's stomach.

3. A method for placing a feeding tube in accordance with claim 1, wherein said placement wire dispenser provided by the providing step further includes an elongated piercing member having a piercing end portion, said piercing member constructed to be removably disposed within said tube of said placement wire dispenser such that said piercing end portion extends outwardly from said first end of said tube, said tube having a second end opposite said first end of said tube, and wherein said piercing member is disposed in said tube when said first end of said tube is placed through a patient's abdominal wall and into a patient's stomach, said method further comprising the step of withdrawing said piercing member from said tube via said second end of said tube.

4. A method for placing a feeding tube in accordance with claim 3, wherein said piercing member provided by the providing step has a hub end portion opposite said piercing end portion, said hub end portion having a hub member mounted thereon.

5. A placement wire dispenser comprising:

a rotatable placement wire receptacle defining a placement wire receptacle outlet therethrough;

a tube extending outwardly from said placement wire receptacle, said tube defining a placement wire tube inlet, said placement wire receptacle outlet and said placement wire tube inlet disposed in communication with one another, said tube having a first end constructed for insertion through a patient's abdominal wall and into a patient's stomach, said tube having a second end constructed for insertion of an elongate piercing member so as to extend outwardly from the first end of said tube; and a placement wire wound about said placement wire receptacle, said placement wire being in mechanical engagement with said placement wire receptacle so rotation of said placement wire receptacle advances a first end portion of said placement wire through said placement wire receptacle outlet and through said tube.

6. A placement wire dispenser in accordance with claim 5, wherein said first end portion of said tube includes a piercing tip constructed for insertion through a patient's abdominal wall and into a patient's stomach.

7. A placement wire dispenser in accordance with claim 5, wherein said placement wire dispenser further comprises an elongated piercing member having a piercing end portion, said piercing member constructed to be removably inserted in the second end of said tube such that said piercing end portion extends outwardly from said first end of said tube.

8. A placement wire dispenser in accordance with claim 7, wherein said piercing member has a hub end portion opposite said piercing end portion, said hub end portion having a hub member mounted thereon.

9. The placement wire dispenser in accordance with claim 5, further comprising a fluid flow valve in said tube, said fluid flow valve constructed to allow the placement wire to be advanced therethrough.

10. The placement wire dispenser in accordance with claim 5, further comprising a removable sheath to surround the first end of said tube.

11. A feeding tube placement kit comprising:

a placement wire dispenser including:

a rotatable placement wire receptacle having a placement wire receptacle outlet defined therethrough, a tube extending outwardly from said placement wire receptacle, said tube having a placement wire tube inlet defined therein, said placement wire receptacle outlet and said placement wire tube inlet disposed in communication with one another, said tube having a first end constructed for insertion through a patient's abdominal wall and into a patient's stomach, and a placement wire wound about said placement wire receptacle, said placement wire being in mechanical engagement with said placement wire receptacle whereby rotation of said placement wire receptacle advances a first end portion of said placement wire through said placement wire receptacle outlet and through said tube; and a feeding tube provided external of the placement wire dispenser, said feeding tube having a first end portion and a second end portion, said feeding tube defining a feeding lumen therethrough, a retention member disposed on said second end portion of said feeding tube.

12. A feeding tube placement kit in accordance with claim 11, wherein said feeding tube is constructed of a polyurethane material.

13. A feeding tube placement kit in accordance with claim 11, wherein said kit further comprises:

an adaptor having an outlet conduit, said outlet conduit constructed for fluid connection with said first end portion of said feeding tube, said adaptor having a first inlet conduit and a second inlet conduit, said first and second inlet conduits being in fluid communication with said outlet conduit.

14. A feeding tube placement kit in accordance with claim 13, wherein said outlet conduit of said adaptor has an exterior surface, said exterior surface of said outlet conduit having a first section with an increasing circumferential dimension from an outlet end of said adaptor to an inlet end of said adaptor, said exterior surface of said outlet conduit having a second section having a decreasing circumferential dimension from an outlet end of said adaptor to an inlet end of said adaptor, said second section positioned closer to said first and second inlet conduits than said first section, said first section and said second section defining a tube retention member on said exterior surface of said outlet conduit.

15. The feeding tube placement kit in accordance with claim 11, further comprising a grasping device constructed to grasp a first end portion of said placement wire when disposed within a patient's stomach.

16. The feeding tube placement kit in accordance with claim 11, further comprising a fluid flow valve in said tube, said fluid flow valve constructed to allow the placement wire to be advanced therethrough.

17. The feeding tube placement kit in accordance with claim 11, further comprising a removable sheath to surround the first end of said tube.

* * * * *